US009283020B2

(12) United States Patent
Drapeau et al.

(10) Patent No.: US 9,283,020 B2
(45) Date of Patent: Mar. 15, 2016

(54) SURGICAL TACK DELIVERY SYSTEM, METHOD AND KIT

(75) Inventors: Susan J. Drapeau, Cordova, TN (US); Kelly Brook Emerton, Memphis, TN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 534 days.

(21) Appl. No.: 12/983,544

(22) Filed: Jan. 3, 2011

(65) Prior Publication Data

US 2012/0172885 A1 Jul. 5, 2012

(51) Int. Cl.
*A61B 17/58* (2006.01)
*A61B 17/60* (2006.01)
*A61F 2/00* (2006.01)
*A61B 17/92* (2006.01)
*A61B 17/86* (2006.01)

(52) U.S. Cl.
CPC ............ *A61B 17/92* (2013.01); *A61B 17/86* (2013.01); *A61B 17/865* (2013.01)

(58) Field of Classification Search
CPC ............ A61B 17/865; A61B 2017/0647; A61B 17/068; A61B 2017/0688; B25B 23/045; B25B 23/06
USPC ......... 227/175.1–182.1; 606/104, 73; 30/367; 173/121, 202; 206/343; 81/44, 463
See application file for complete search history.

(56) References Cited

U.S. PATENT DOCUMENTS

| 3,172,204 | A  | * | 3/1965  | Frey ............................... 30/367 |
| 4,527,726 | A  |   | 7/1985  | Assell et al. |
| 4,540,110 | A  |   | 9/1985  | Bent et al. |
| 4,577,400 | A  |   | 3/1986  | Morgan |
| 4,998,452 | A  | * | 3/1991  | Blum ........................... 81/57.37 |
| 5,231,900 | A  | * | 8/1993  | Deri ............................ 81/57.37 |
| 5,568,753 | A  | * | 10/1996 | Habermehl et al. ............ 81/434 |
| 5,741,268 | A  | * | 4/1998  | Schutz ........................ 606/104 |
| 5,921,456 | A  |   | 7/1999  | Kirsch et al. |
| 6,010,508 | A  |   | 1/2000  | Bradley |
| 6,129,731 | A  | * | 10/2000 | Haeusler et al. ................ 606/79 |
| 6,402,759 | B1 |   | 6/2002  | Strong et al. |
| 6,830,573 | B2 | * | 12/2004 | Strong et al. .................. 606/300 |
| 6,902,093 | B1 |   | 6/2005  | Chang |
| 7,104,994 | B1 |   | 9/2006  | Amis et al. |
| 7,147,641 | B2 | * | 12/2006 | Chen ............................ 606/104 |
| 7,338,494 | B2 |   | 3/2008  | Ryan |
| 7,530,458 | B2 | * | 5/2009  | Fujiyama et al. ............. 206/345 |
| 2002/0193807 | A1 |   | 12/2002 | Chen |
| 2008/0149511 | A1 | * | 6/2008  | Pleil et al. ..................... 206/339 |
| 2009/0036897 | A1 |   | 2/2009  | Fitzpatrick et al. |
| 2011/0203417 | A1 | * | 8/2011  | Hill, III ............................. 81/44 |
| 2012/0109142 | A1 | * | 5/2012  | Dayan .......................... 606/104 |

OTHER PUBLICATIONS

Biohorizons Inc., Global Headquarters, 2300 Riverchase Center, Birmingham, AL 35244, USA Auto-Tac® Membrane fixation system Copyright 2010 BioHorizons, Inc. www.biohorizons.com/autotac.aspx.

* cited by examiner

*Primary Examiner* — Kevin T Truong
*Assistant Examiner* — Si Ming Ku
(74) *Attorney, Agent, or Firm* — Sorell Lenna & Schmidt LLP (57) ABSTRACT

A system for delivering a surgical tack in tissue includes a driver, including: a shaft having a slot and a channel; and a handle slidably connected to the shaft and having a driving mechanism, the driving mechanism having a driving pin for providing a downward force through the shaft; and a tack cartridge having a plurality of tacks and adapted to be received in the slot and further adapted to feed the tacks between the driving mechanism and the channel.

28 Claims, 5 Drawing Sheets

SURGICAL TACK DELIVERY SYSTEM, METHOD AND KIT

TECHNICAL FIELD

The present disclosure generally relates to medical devices for securing and spacing, and more particularly to a surgical tack delivery system, method and kit for securing membranes or maintaining spaces in dental and orthopedic applications.

BACKGROUND

Surgical tacks can be used in dental and orthopedic applications for securing membranes, maintaining spaces, etc. Traditional delivery methods rely on mallet delivery while the physician holds a surgical tack in place with a forceps. The process of holding the surgical tack in place and providing a driving force thereto with the mallet results in an application of unpredictable force and accuracy. The process requires both hands of the installer to install the surgical tack.

SUMMARY OF THE INVENTION

Accordingly, a surgical tack delivery system, method and kit are provided.

In one embodiment, in accordance with the principles of the present disclosure, a system for delivering surgical tack is provided. The system includes a driver, comprising: a shaft having a slot and a channel; and a handle slidably connected to said shaft and having a driving mechanism, said driving mechanism having a driving pin for providing a downward force through said shaft; and a tack cartridge having a plurality of tacks and adapted to be received in said slot and further adapted to feed said tacks between said driving mechanism and said channel.

In another embodiment, in accordance with the principles of the present disclosure, a method for delivering a surgical tack is provided. The method includes providing a driver containing a tack cartridge having a plurality of tacks contained therein, said driver having a driving mechanism and a shaft, said shaft having a channel at a distal end thereof, wherein when said tack cartridge is inserted into said slot a first tack of said plurality of tacks is aligned with said driving mechanism and said channel; placing a distal end of the channel at a location of a tissue at which a first tack is to be inserted; providing pressure on the handle in the direction of the distal end of the channel, said pressure providing a driving force for said driving mechanism, said driving force being transferred to said first tack to drive said first tack into said piece of work; and moving a second tack into alignment with said driving mechanism and said shaft.

In yet a further embodiment, in accordance with the principles of the present disclosure, a kit for delivering a surgical tack is provided.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments of the surgical tack delivery system disclosed are discussed in terms of medical devices for dental and/or orthopedic applications for securing membranes and/or maintaining spaces.

It is envisioned that the surgical tack delivery system disclosed provides a reliable and safe access to a dental or orthopedic region to secure membranes and/or maintain spaces. It is further envisioned that the surgical tack delivery system is configured to deliver one or more tacks to the dental or orthopedic region to securing membranes and/or maintaining spaces.

The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a surgical tack delivery system in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there are illustrated components of a surgical tack delivery system 10 in accordance with the principles of the present disclosure.

Figure 2:
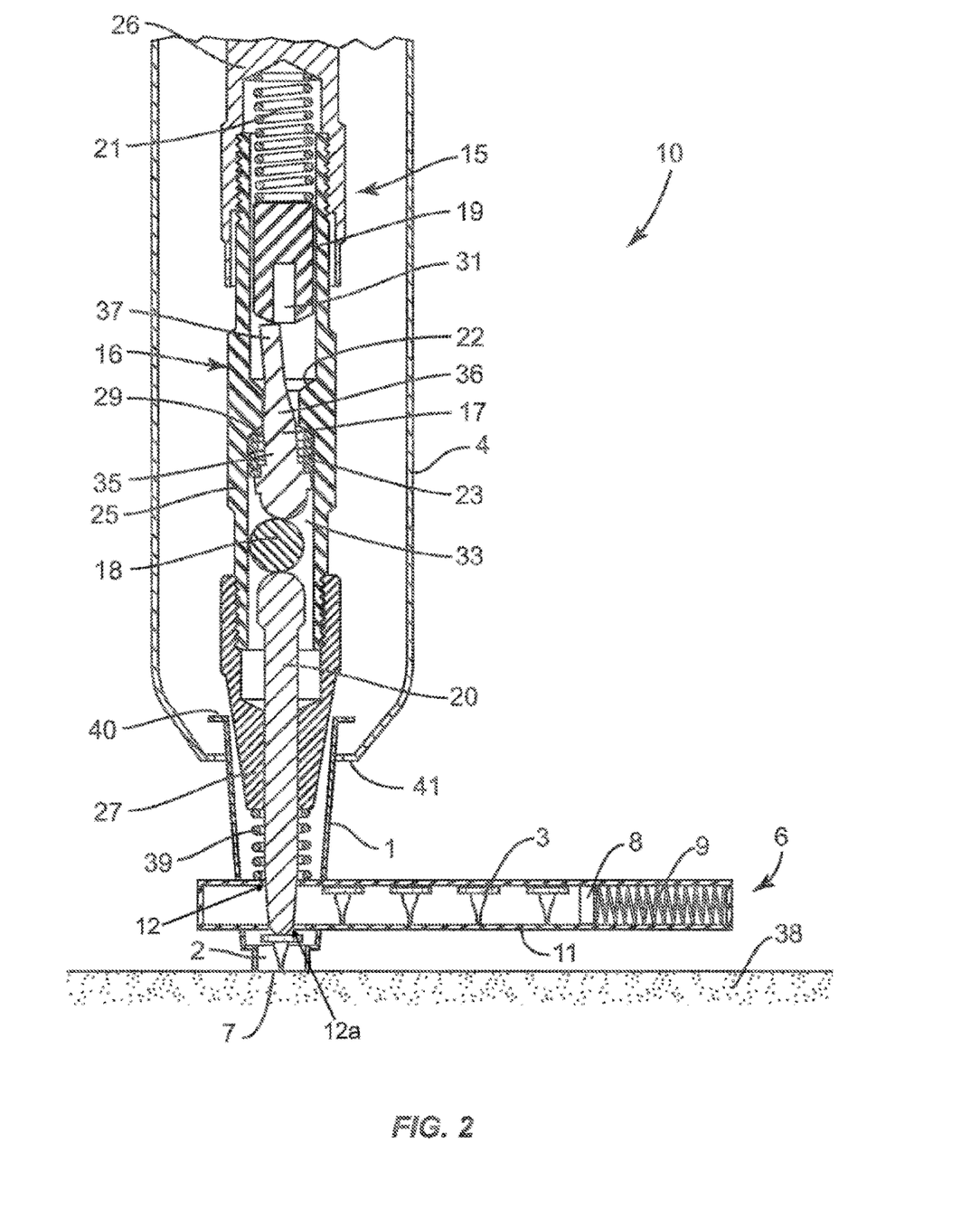
FIG. 2 is a cross section view of a tack delivery system in its pressure condition in accordance with the principles of the present disclosure.
Figure 3:
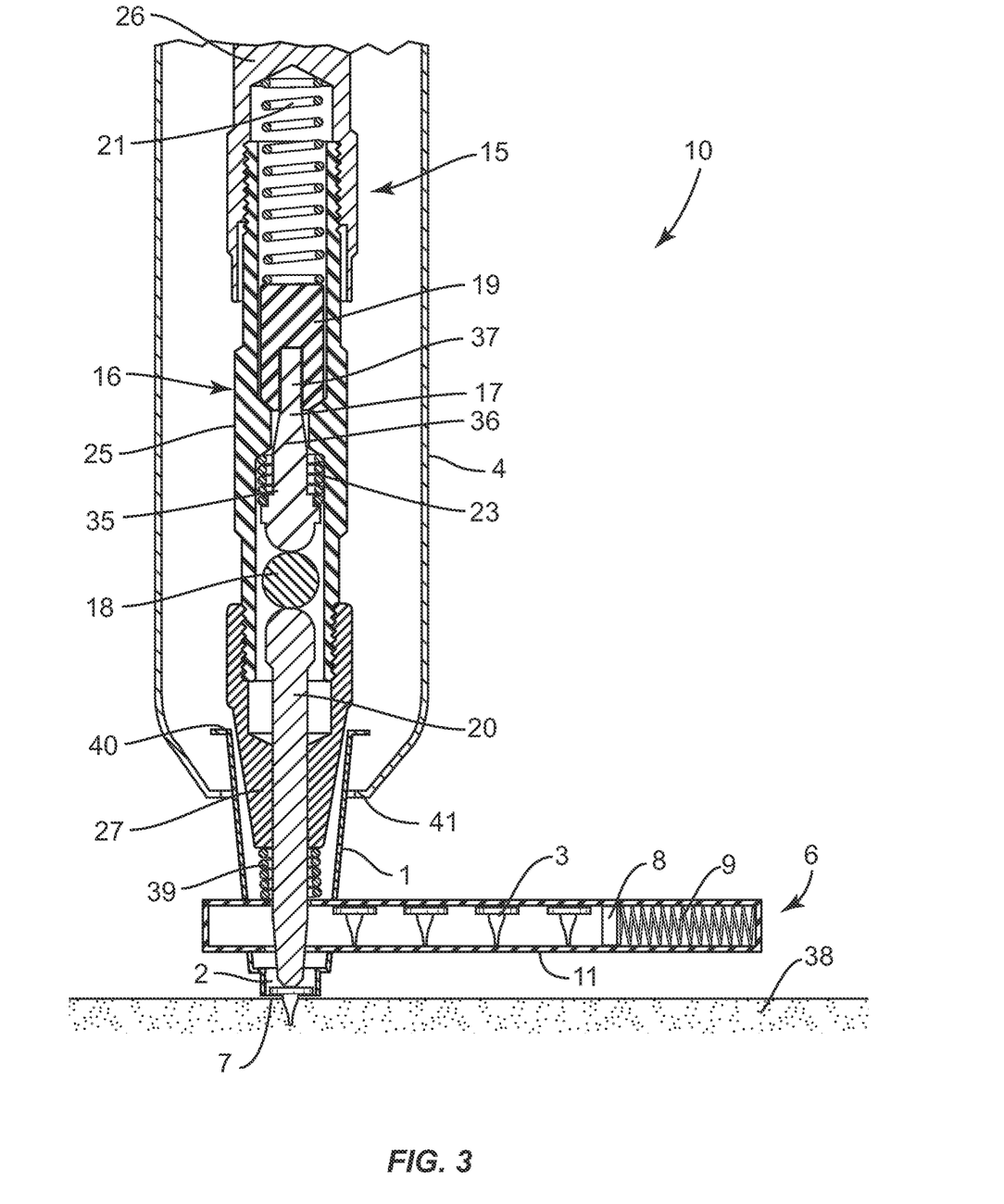
FIG. 3 is a cross section view of a tack delivery system in its tack insertion condition in accordance with the principles of the present disclosure.

Surgical tack delivery system 10 is configured to deliver a tack in dental and/or orthopedic application for securing membranes and/or maintaining spaces. The invention relates to a system for attaching tacks to bone, having a shaft 1 with a channel 2 extending therefrom and adapted to receive a tack 3. The upper end of the shaft 1 includes a shaft lip 40. The shaft 1 extends upward into a handle 4. The lower end of the handle has a handle lip 41. Shaft 1 and handle 4 are slidably connected and, at rest, shaft lip 40 and handle lip 41 are in contact and prevent shaft 1 from separating from handle 4. Spring 39 provides a force to maintain contact between shaft lip 40 and handle lip 41 in the at rest position. Shaft 1 has a slot 5 that is in communication with the shaft 1. The slot 5 is adapted to receive a tack cartridge 6. The tack cartridge 6 is adapted to include a plurality of tacks 3. The handle 4 includes a driving mechanism 15 to apply a force in the direction of the shaft 1 to a head of a tack 3 in the tack cartridge 6. When the tack cartridge 6 is inserted into the slot 5, a tack 3 is aligned with the channel 2 and the driving mechanism 15. When a distal end 7 of the shaft 1 is placed against a location at which a tack is to be installed and pressure is applied to the handle 4 in a direction of the shaft 1, the pressure compresses spring 39 and pushes driving mechanism 15 onto tack 3. As shown in FIG. 2, continued pressure pushes driving mechanism 15 to push tack 3 into channel 2 and onto surface of work piece 38 (e.g. bone). Then as shown in FIG. 3, the driving mechanism 15 applies its force to direct the tack 3 into the bone 38. As the pressure is released, spring 39 provides a force to return shaft 1 and handle 4 to their at rest positions. In its return to the at rest position, as driving mechanism clears the slot 5, the tack cartridge 6 advances tacks 3 to align another tack 3 with the channel 2 and the driving mechanism 15.

In a preferred embodiment all parts are of circular cross section and hence easily made. The surgical tack delivery system 10 comprises an elongated tubular casing 16, which houses an elongated plunger 17 between an unattached ball 18 and a slidable hammer member 19, and also has a retractable bit 20; said ball being between said plunger 17 and said retractable bit 20. A compression coil spring 21 biases said hammer member 19 towards said plunger and forces said hammer member to normally rest against a seat 22. A second compression coil spring 23, biases said plunger 17 against said ball 18, and hence said ball bears against the butt end head 24 of said pointed bit. A third compression coil spring 35, biases said retractable bit 20 against said ball 18.

Figure 1:
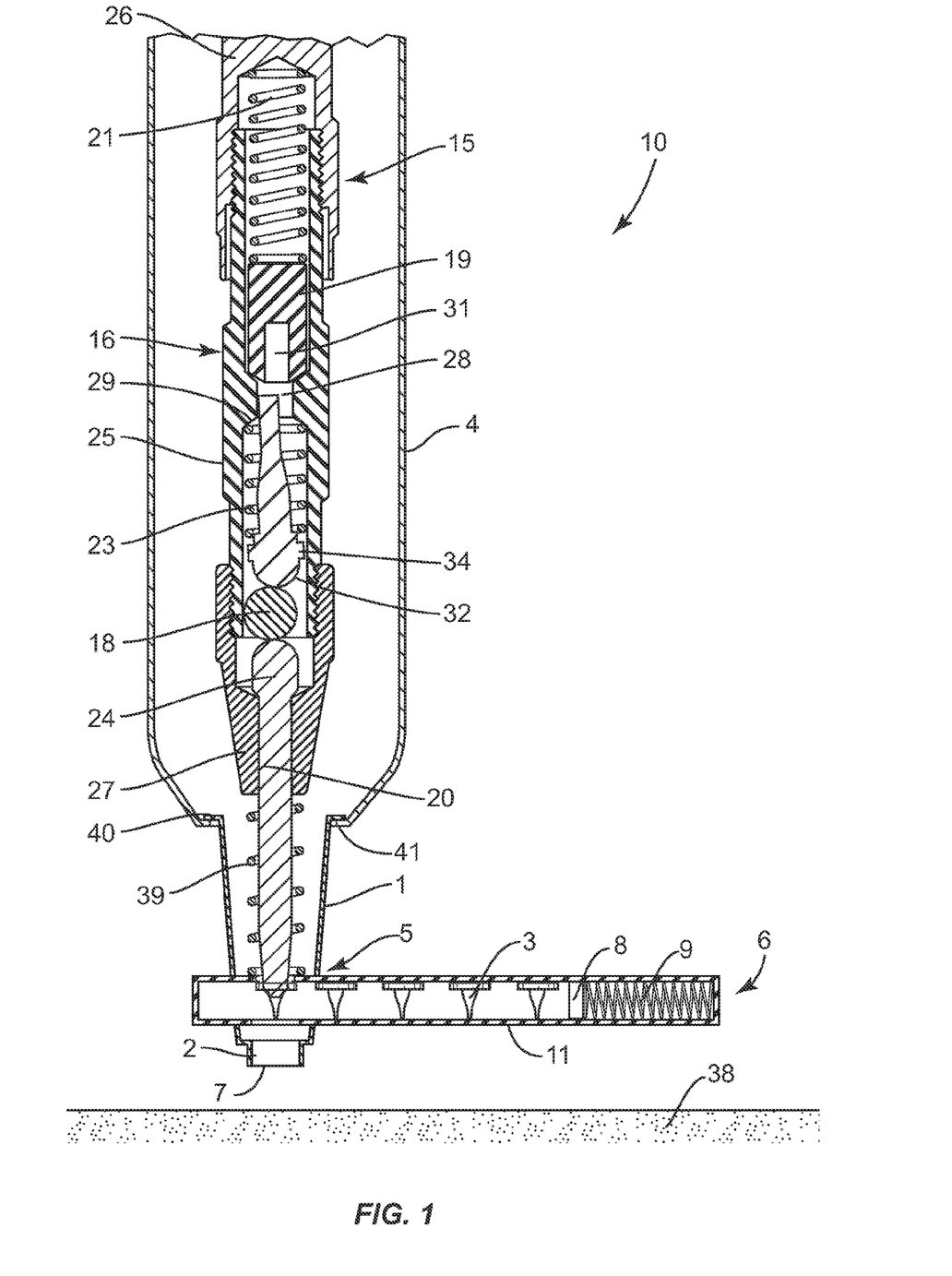
FIG. 1 is a cross section view of a tack delivery system in its normal rest condition in accordance with the principles of the present disclosure.

The casing 16 consists of the tubular member 25, which at hammer-end is closed by a cap 26, serving as an anchor for the coil spring 21 which bears against said hammer member 19, and said tubular member 25 has an extension 27 at its other end which serves as the slide bearing for the retractable bit 20; said cap and extension, being threadedly engaged to the respective ends of said tubular member 25, to permit adjustment of the initial stress in said springs 21 and 23 respectively. Said member 25 has a constricted passage 28 intermediate its ends, thereby offering the seat 22, and as an anchorage for the coil spring 23, the seat 29. The constriction 28 is of circular cross section and is co-axial with the hammer member 19, the latter's socket 31, and the retractable bit 20. The head 32 of the plunger 17 that bears against the ball 18, and the distal end of the head 24 of the retractable bit 20, are semi-spherical in shape and of a diameter preferably slightly less than that of the ball 18. The diameter of said ball must be such in relation to the diameter of the bore 33 it is in, that the plunger 17 and the retractable bit 20 shall never contact each other. It is best that the ball's diameter be more than the radius of said bore 33. It is essential that dimensions be so chosen that when the tool 15 is in normal rest condition as shown in FIG. 1, the plunger 17 shall be slanted to the axis line of the hammer member 19 and preferably bear against the wall of the constricted passage 28. It is suggested that the diameter of said ball 18 shall be a minimum of 10% larger than the radius of said bore 33 and a minimum of 10% smaller than the diameter of said bore.

The plunger 17, near head end, has a flange 34 to seat the coil spring 23, and from there, has three successive sections indicated by the numerals 35, 36 and 37 respectively. The section 35 is of a diameter adapted to slidably fit in the constricted passage 28. The stem section 37 is of a reduced diameter adapted to slidably fit into the hammer's socket 31. The section 36 is frustoconical and merges with said other sections. The spring 23 which biases the plunger 17, is relatively weak as compared with the comparatively strong spring 21 which biases the hammer member 19.

Although a mechanical spring-loaded driving mechanism is illustrated, other driving mechanisms are contemplated. Whichever particular driving mechanism is utilized, a driving force is applied to set a tack into the bone.

Figure 7:
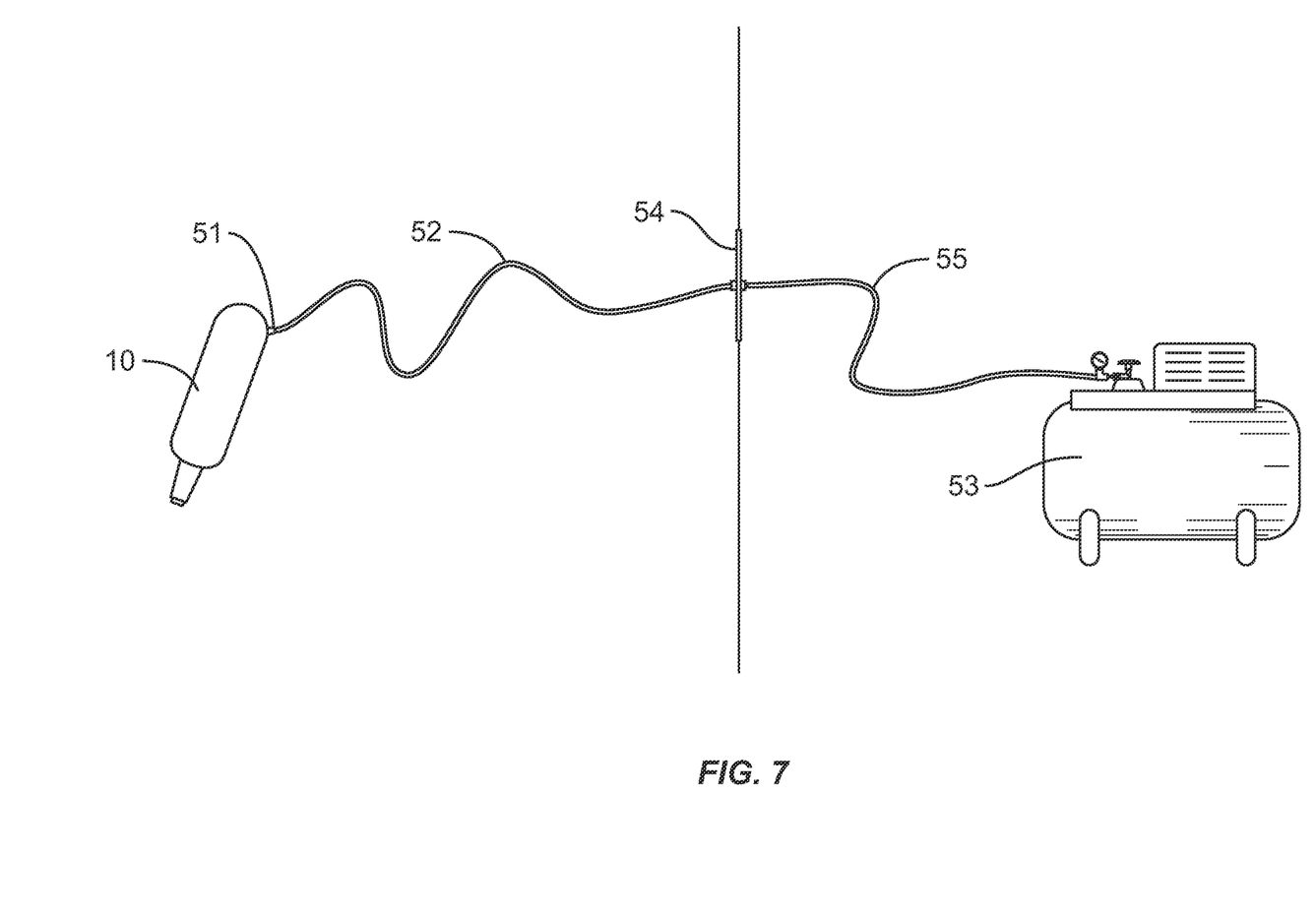
FIG. 7 is a diagram illustrating a tack delivery system according to an embodiment of the present invention.

In one alternate embodiment of the present invention, a pneumatic driving mechanism is utilized. The pneumatic driving mechanism utilizes pressurized gas or air to provide the driving force to the retractable bit 20. The air for the pneumatic driving mechanism can be supplied by any of various well-known systems, including, but not limited to, cartridge-based pneumatic systems, compressor-based pneumatic systems, or pump-action pneumatic systems. A compressor-based pneumatic system is shown in FIG. 7. Many hospital operating rooms include access to compressed air generated by an air compressor 53. The surgical tack delivery system 10 can include an air hose connection 51 that in turn can be connected to an air hose 52. Air hose 52 can attach to an air compressor 53 through various means, including wall plate 54 and hose 55. The compressed air supplied from air compressor 53 can be used to supply the driving force to the retractable bit 20 to drive a tack 3 into the work piece 38. Whichever pneumatic system is used, the single-handed operation of the surgical tack delivery system 10 is still maintained.

To operate the surgery tack delivery system 10, it is set so that the distal end 7 of the shaft 1 is on that point on the surface 38 of a bone at which a tack 3 is to be inserted. The surgical tack delivery system 10 is in the condition shown in FIG. 1. Now, the handle 4 is pressed towards the bone, whereupon as shown in FIG. 2, more of the retractable bit 20 will move into the casing, thereby causing the plunger 17 to shift against the hammer member 19, and move it away from the seat 22. In addition, handle 4 will slide down over shaft 1. Springs 21, 23 and 39 will become compressed and upon continuing such movement of the casing, the plunger 17 will be cammed and get into alignment with the hammer member 19, whereupon the hammer will be freed to be forced by the fully stressed spring 21, to move towards the retractable bit 20, because the plunger section 37 will enter the socket 31 and receive the hammer's blow as shown in FIG. 3. The impact will be transmitted to the retractable bit 20 and onto the tack 3 and forcing the tack 3 into the bone. Upon removal of the pressure on the handle, the stressed spring 23 will restore the plunger 17, and hence also the ball 18 and the retractable bit 20, to normal rest position as shown in FIG. 1, and the tool will then again be ready for its next use.

When as in FIG. 3, the plunger 17 comes into axial alignment with the hammer 19, the ball 18 is never in such alignment, and it is found that upon every operation of surgical tack delivery system 10, that said ball 18 will receive some turning movement and change its position along the wall of the bore 33. Hence, the points of impact of said ball and plunger head 32 and the points of impact of said ball and the bit's head 24, change from one stroke of the tool to the next, thereby eliminating wear on just definite points as was the experience in prior devices of this class.

It is to be particularly noted that the ball 18 will always position the plunger 17 off center and to a slant position as shown in FIG. 1, when the retractable bit 20 extends its maximum out of the casing 16, and such action is not effected when the butt end of said bit is flat instead of semi-spherical as herein shown.

Figure 4:
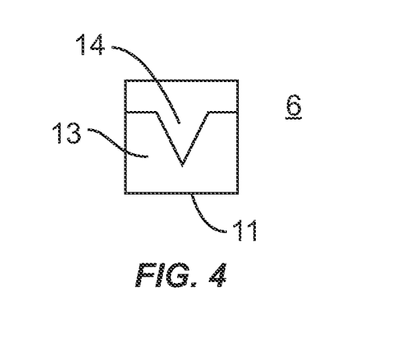
FIG. 4 is a cross sectional diagram of a tack cartridge in accordance with the principles of the present disclosure.
Figure 5:
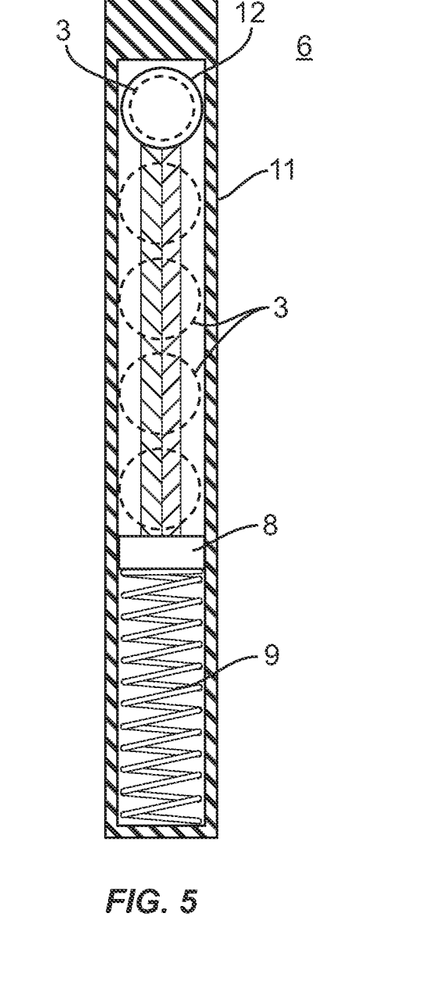
FIG. 5 is a plane view of a tack cartridge in accordance with the principles of the present disclosure.
Figure 6:
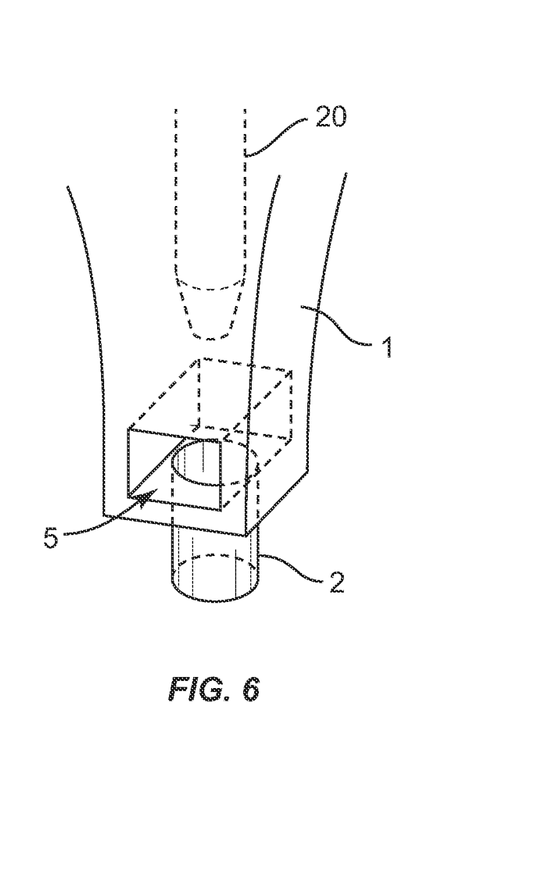
FIG. 6 is an enhanced view of a handle of a tack delivery system showing a tack cartridge slot.

The tack cartridge 6 is comprised of a casing 11 having a tack guide 13 formed therein. A spacing 14 shaped to fit a tack 3 is included in the casing 11. Plunger 8 is biased by spring 9 to apply a force in the direction of hole 12 and hole 12a. As tacks 3 are loaded into the tack cartridge 6, plunger 8 compresses spring 9. When the tack cartridge 6 is inserted into slot 5, hole 12 and hole 12a align with shaft 1 to allow for a tack 3 to be driven from the tack cartridge 6 down through shaft 1. When a tack 3 is ejected from the tack cartridge 6 by driving mechanism 15, plunger 8 forces remaining tacks 3 toward hole 12 and hole 12a until a foremost tack 3 is centered in hole 12 and hole 12a. Hole 12 and hole 12a are pass-through holes.

In another embodiment of the present invention, the surgical tack delivery system 10 can be modified in a manner such that the retractable bit 20 stabilizes the tack 3 at the work piece 38. In order to accomplish the stabilization, the retractable bit 20 can be modified. In one such example, the retractable bit 20 can be magnetized and the tack 3 can be composed of a magnetic material; thus when contact is made between the retractable bit 20 and the tack 3, the tack will remain attached thereto until embedded into the work piece 38; this allows for one-handed operation of the tack delivery system, even without the use of the tack cartridge 6. In another example, the retractable bit 20 can include a suction tip to provide an attaching force between the retractable bit 20 and the tack 3; the suction tip can be a small suction cup that has a diameter less than the diameter of a head of a tack 3; thus when the suction force is applied between the retractable bit 20 and the tack 3, the tack will remain attached thereto until embedded into the work piece 38; this again allows for one-handed operation of the tack delivery system, even without the use of the tack cartridge 6. And in yet another example, the retractable bit 20 can include an interference/slip-fit end that can mate with a tack 3; the interference/slip-fit end can be a recess in the retractable bit 20 the inside diameter of which is greater than the diameter of a head of a tack 3, such that the head of the tack 3 fits somewhat snuggly into the recess in the retractable bit 20; thus when the tack 3 is fitted into the recess of the retractable bit 20, the tack will remain stabilized until embedded into the work piece 38; this yet again allows for one-handed operation of the tack delivery system, even without the use of the tack cartridge 6. Although several examples have been described, the concept of providing a stabilizing force between the retractable bit 20 and the tack 3 can allow for one-handed operation of the surgical tack delivery system 10.

Another embodiment of the present invention is directed to a method for delivering a surgical tack to a site in a surgical procedure. The method comprises providing a driver containing a tack cartridge having a plurality of tacks contained therein. The cartridge can be inserted at the time of use or the driver can be provided with the cartridge preloaded. Once the driver and the cartridge is positioned in place, the driving mechanism and a shaft of the driver provides pressure on the handle in the direction of the distal end of the channel of the driver. The pressure provides a driving force for the driving mechanism and the driving force is transferred to the first tack in the cartridge to drive the first tack into the tissue and/or membrane. Once this is completed a second tack is automatically or manually moved into alignment with the driving mechanism and said shaft so that the next tack can be delivered. This procedure is repeated until no more tacks are needed or until the cartridge is depleted of tacks. In latter case, another cartridge can be inserted and the process repeated.

Assembly, operation and use, of the surgical tack delivery system is employed with a surgical procedure for treatment of a spine of a patient including vertebrae V, intervertebral disc I and body areas adjacent thereto, as discussed herein. The surgical tack delivery system may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and membranes, as well as various dental procedures.

In use, the surgical tack delivery system of the present invention, a medical practitioner obtains access to a surgical site in any appropriate manner, such as through incision and retraction of tissues. It is envisioned that the surgical tack delivery system may be used in any existing surgical method or technique including open surgery, mini-open surgery, minimally invasive surgery and percutaneous surgical implantation, whereby the surgical site is accessed through a mini-incision, or sleeve that provides a protected passageway to the area. Once access to the surgical site is obtained, the particular surgical procedure is performed for treating the disorder. The surgical tack delivery system is then employed to augment the surgical treatment. It is contemplated that the surgical tack delivery system can be used and manipulated by the surgeon using a single hand thereby leaving the other hand of the surgeon free.

The components of surgical tack delivery system and the tacks used therein can be fabricated from materials suitable for medical applications, including metals, polymers, ceramics, biocompatible materials, tissues, and/or their composites, depending on the particular application and/or preference of a medical practitioner. For example, the components of surgical tack delivery system, individually or collectively, and which may be monolithically formed or integrally connected, can be fabricated from materials such as stainless steel, stainless steel alloys, titanium, titanium alloys, super-elastic titanium alloys, cobalt-chrome alloys, shape memory materials, such as super-elastic metallic alloys (e.g., Nitinol, super-elastic plastic metals, such as GUM METAL® manufactured by Toyotsu Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, biocompatible materials such as polymers including plastics, metals, ceramics and composites thereof, rigid polymers including polyphenylene, polyamide, polyimide, polyetherimide, polyethylene, and epoxy. Various components of surgical tack delivery system may have material composites, including the above materials, to achieve various desired characteristics such as strength, rigidity, elasticity, compliance, degradability, biomechanical performance, durability and radiolucency or imaging preference. Components alternatively could be prepared from allogeneic or xenogeneic tissues, tissue composites, or biomaterial/tissue composites.

The surgical tacks of the surgical tack delivery system can be coated or dusted with a particulate material, which may include an osteoconductive material such as hydroxyapatite and/or osteoinductive agent such as a bone morphogenic protein to enhance bone growth. The hydroxyapatite may be contained within tack material as a nanocrystalline particulate or coating.

It is contemplated that the tacks used in the delivery system may include therapeutic antibiotics, polynucleotides or polypeptides, which can be packed or otherwise disposed on or within the tacks. It is further contemplated that the tacks may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within a patient. Suitable biologically active agents include, for example, bone morphogenic protein (BMP), Growth and Differentiation Factors proteins (GDF) and cytokines.

In one embodiment, the surgical tacks are fabricated from a resorbable material. It is contemplated that the tacks are fabricated from a biodegradeable material that resorbs over time in vivo. Examples of such include, but are not limited to, polyglycolide, polylactide, polycaprolactone, poly(ethylene glycol), polyurethanes, polyfumarates, polyacrylamides, collagen, silk, polyamines, polysaccharides, tissue or tissue products, and copolymers and blends thereof. It is further contemplated that struts 22, 30 can be adjusted and/or trimmed to the configuration and dimension requirements of a particular application.

In one embodiment, a driver as well as a plurality of preloaded cartridges or free tacks that can be inserted into a reloadable cartridge of various configurations and sizes may be packaged as a system or kit that includes additional bone graft growth material. In such an embodiment, the kit may include one or a plurality of cartridges, free tacks, drivers, and other materials for treatment.

In one embodiment, biologically active agents may be coated onto the exterior of one or all of the tacks and/or applied thereto for gradual release such as by blending in a bioresorbable polymer that releases the biologically active agent or agents in an appropriate time dependent fashion as the polymer degrades within a patient. Suitable biologically active agents include, for example, bone morphogenic protein (BMP) and cytokines.

One or all of the components of tacks may include one or a plurality of agents that can be configured as drug depots with medication for pain and may include antibiotics and/or therapeutics. It is envisioned that the agents may contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A system for delivering a surgical tack in tissue, the system comprising:
   a driver, comprising:
   a shaft having a slot and a channel defining a longitudinal axis, said slot extending entirely through a distal end of said shaft, said shaft comprising a shaft lip extending transverse to said longitudinal axis; and
   a handle slidably connected to said shaft such that said shaft extends upward into said handle, said handle having a driving mechanism and a handle lip extending transverse to said longitudinal axis, said driving mechanism having a driving pin for providing a downward force through said shaft, a top surface of the handle lip is configured to directly contact a bottom surface of the shaft lip;
   a tack cartridge comprising a passageway defined by upper and lower surfaces of said tack cartridge, said upper and lower surfaces including pass-through holes at one end of said tack cartridge, said passageway having a plurality of tacks disposed therein, said tack cartridge being positioned in said slot such that the shaft is in alignment with said pass-through holes, said tack cartridge being adapted to feed said tacks between said driving mechanism and said channel; and
   a spring engaging said tack cartridge and surrounding a portion of said driving pin such that said spring provides a force to maintain contact between said shaft lip and said handle lip,
   wherein said driving pin is movable between a first position in which said driving pin engages one of said tacks within said passageway and a second position in which said driving pin engages said one of said tacks within said channel.

2. The system for delivering a tack of claim 1, wherein the driving mechanism is pneumatically driven.

3. The system for delivering a tack of claim 1, wherein the driving mechanism is spring loaded.

4. The system for delivering a tack of claim 3, wherein the driving mechanism comprises:
  a tubular casing having a constriction intermediate its ends forming a camming element;
  a bit slidable in said casing at one side of said constriction and protruding from said casing, said bit having a first semi-spherical head at its end which is interior said casing, said casing at said one side of said constriction, being of circular cross-section internally;
  a separate ball within said casing, bearing against said first semi-spherical head;
  a plunger of circular cross-section including a second semi-spherical head bearing against said ball;
  a stem extending into said constriction and a tapered cam portion on said stem, adapted as said stem is urged through said constriction, to engage said camming element and move the extremity of said stem remote from said second semi-spherical head, from a position offset with respect to a longitudinal axis defined by said casing, to a centered position in alignment with the longitudinal axis;
  a hammer member slidable in said casing on a side of said constriction opposite said one side of said constriction;
  a second spring biasing said hammer member towards said constriction, an inward end of said hammer member being adapted to be engaged by said stem when in its offset position and a socket in said inward end of said hammer member, adapted to receive said stem when said stem is in its aligned position whereby on receiving said stem, the hammer member is driven by said second spring into impact engagement therewith; and
  a third spring biasing said plunger towards said ball, a diameter of said ball being smaller than a diameter of said cross-section of the casing and larger than diameters of said semi-spherical heads respectively, said ball being of a diameter so that said plunger remains spaced from said bit.

5. The system for delivering a surgical tack in tissue of claim 1, wherein the tack cartridge comprises:
  a tack guide adapted for guiding tacks through the tack cartridge, said tack guide defining a V-shaped spacing configured for disposal of portions of said tacks;
  a plunger positioned behind the tacks and configured for moving at least one tack within said tack guide toward said pass-through holes; and
  a resilient member for applying a moving force to said plunger.

6. The system for delivering a tack of claim 5, wherein a shape of the tack guide conforms to a shape of a tack.

7. The system for delivering a tack of claim 1, further comprising a plurality of tack cartridges, each of said tack cartridge includes a different size of tack.

8. The system for delivering a tack of claim 1, further comprising:
  a casing comprising an inner surface defining a first passageway, an outer surface of said casing comprising a first thread form; and
  an extension comprising an inner surface defining a second passageway that is aligned with the first passageway, the inner surface of the extension comprising a second thread form,
  wherein said driving mechanism comprises a plurality of springs and said first thread form is movable relative to said second thread form to adjust said force of said driving mechanism.

9. The system for delivering a tack of claim 1, wherein said force is preset for driving a tack into bone.

10. The system for delivering a tack of claim 1, wherein the driving pin is magnetized to provide a magnetic attraction force to a tack.

11. The system for delivering a tack of claim 1, wherein a suction force is applied between the driving pin and a tack.

12. The system for delivering a tack of claim 1, a distal end of the driving pin is formed to mate with a head of a tack.

13. A kit for delivering a tack, comprising:
  the system for delivering a tack of claim 1; and
  a plurality of tack cartridges containing tacks of varying sizes.

14. The kit for delivering a tack of claim 13, wherein said system and said plurality of tack cartridges are disposable.

15. The kit for delivering a tack of claim 13, wherein said system and said plurality of tack cartridges are in a sterilized package.

16. The kit for delivering a tack of claim 13, wherein said kit is sterilized.

17. The system for delivering a tack of claim 1, wherein said spring compresses and pushes said driving mechanism onto one of said tacks when said distal end of said shaft is placed against a location at which one of said tacks is to be installed.

18. The system for delivering a tack of claim 1, wherein:
  said shaft lip contacts said handle lip when said shaft lip and said handle lip are in a rest position; and
  releasing pressure from said spring moves said shaft lip and said handle lip into the rest position.

19. The system for delivering a tack of claim 18, wherein a portion of said spring is positioned within said shaft and a portion of said spring is positioned within said handle when said shaft lip and said handle lip are in the rest position.

20. The system for delivering a tack of claim 1, wherein:
  said shaft lip contacts said handle lip when said handle is in a rest position; and
  said shaft is movable relative to said handle from the rest position to an installation position in which said shaft lip is spaced apart from said handle lip.

21. The system for delivering a tack of claim 20, wherein said spring is positioned entirely within said shaft when said handle is in said installation position.

22. The system for delivering a tack of claim 1, further comprising a casing surrounding at least a portion of said driving mechanism, said casing comprising an extension, wherein a first end of said spring engages a lower surface of said extension and a second end of said spring engages said upper surface of said tack cartridge.

23. The system for delivering a tack of claim 1, wherein a lower surface of said shaft lip engages an upper surface of said handle lip when said shaft lip contacts said handle lip, said lower surface of said shaft lip facing said tack cartridge.

24. The system for delivering a tack of claim 1, wherein said slot extends through opposite sides of said shaft.

25. The system for delivering a tack of claim 1, wherein said tack cartridge extends completely through said shaft such that one end of said tack cartridge extends outwardly from one side of said shaft and an opposite end of said tack cartridge extends outwardly from an opposite side of said shaft.

26. The system for delivering a tack of claim 1, wherein said pass-through holes comprise a proximal pass-through hole and a distal pass-through hole, said distal pass-through hole having a maximum diameter that is greater than that of said proximal pass-through hole.

27. A system for delivering a surgical tack in tissue, the system comprising:
a driver, comprising:
a shaft having a slot and a channel, said slot extending entirely through a distal end of said shaft, said shaft comprising a shaft lip; and
a handle slidably connected to said shaft such that said shaft extends upward into said handle, said handle having a driving mechanism and a handle lip, said driving mechanism having a driving pin for providing a downward force through said shaft; a tack cartridge comprising a passageway defined by upper and lower surfaces of said tack cartridge, said upper and lower surfaces including pass-through holes at one end of said tack cartridge, said passageway having a plurality of tacks disposed therein, said tack cartridge being positioned in said slot such that the shaft is in alignment with said pass-through holes, said tack cartridge being adapted to feed said tacks between said driving mechanism and said channel; and
a spring engaging said tack cartridge and surrounding a portion of said driving pin such that said spring provides a force to maintain contact between said shaft lip and said handle lip,
wherein said driving pin is movable between a first position in which said driving pin engages one of said tacks within said passageway and a second position in which said driving pin engages said one of said tacks within said channel, and
wherein said shaft lip contacts said handle lip when said handle is in a rest position and said shaft is movable relative to said handle from the rest position to an installation position in which said shaft lip is spaced apart from said handle lip.

28. A system for delivering a surgical tack in tissue, the system comprising:
a driver, comprising:
a shaft having a slot and a channel, said slot extending entirely through a distal end of said shaft, said shaft comprising a shaft lip; and
a handle slidably connected to said shaft such that said shaft extends upward into said handle, said handle having a driving mechanism and a handle lip, said driving mechanism having a driving pin for providing a downward force through said shaft;
a tack cartridge comprising a passageway defined by upper and lower surfaces of said tack cartridge, said upper and lower surfaces including pass-through holes at one end of said tack cartridge, said passageway having a plurality of tacks disposed therein, said tack cartridge being positioned in said slot such that the shaft is in alignment with said pass-through holes, said tack cartridge being adapted to feed said tacks between said driving mechanism and said channel, said tack cartridge extending completely through said shaft such that one end of said tack cartridge extends outwardly from one side of said shaft and an opposite end of said tack cartridge extends outwardly from an opposite side of said shaft; and
a spring engaging said tack cartridge and surrounding a portion of said driving pin such that said spring provides a force to maintain contact between said shaft lip and said handle lip,
wherein said driving pin is movable between a first position in which said driving pin engages one of said tacks within said passageway and a second position in which said driving pin engages said one of said tacks within said channel.

* * * * *